(12) United States Patent
Cheng et al.

(10) Patent No.: US 6,235,941 B1
(45) Date of Patent: May 22, 2001

(54) PROCESS FOR PRODUCTION OF ORGANIC DISULFIDES

(75) Inventors: Chi Hung Cheng; Gerald M. Sulzer, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/619,164

(22) Filed: Feb. 13, 1998

(51) Int. Cl.[7] .................. C07C 321/00; C07C 321/12
(52) U.S. Cl. .............................................. 568/26; 568/21
(58) Field of Search ..................... 568/21, 25, 26

(56) References Cited

U.S. PATENT DOCUMENTS 2,859,249  *  11/1958  Haimsohn et al. .
5,659,086     8/1997  Pauwels et al. .................. 568/26

* cited by examiner

*Primary Examiner*—Jean F. Vollano
(74) *Attorney, Agent, or Firm*—Philip M. Pippenger

(57) ABSTRACT

An aqueous solution of basic mercaptide salt and water-soluble peroxide are mixed together in a reaction zone and maintained under reaction conditions effective to produce a vapor phase comprising organic disulfide, and concurrently vapor phase is recovered from the reaction zone. The process is highly efficient and enables production of organic disulfides in high yield and purity. Not only is the process very easy and simple to carry out, but in addition the process (i) eliminates the need for forming an organic phase of liquid organic disulfide product and conducting a separation between such product and the total aqueous phase used in the reaction, (ii) enables efficient control of a highly exothermic reaction, and (iii) minimizes alkanesulfonic acid salt formation during the reaction.

40 Claims, 1 Drawing Sheet

US 6,235,941 B1

PROCESS FOR PRODUCTION OF ORGANIC DISULFIDES

TECHNICAL FIELD

This invention relates to an improved process by which organic disulfides, especially lower alkyl disulfides, can be produced in high yield and with high efficiency.

BACKGROUND

U.S. Pat. No. 5,659,086 describes a process for producing organic disulfides comprising the steps of (1) contacting a base and a mercaptan to form a brine phase comprising the base and a basic salt of a mercaptan; (2) contacting the brine phase with a mercaptan and hydrogen peroxide to form an aqueous phase and an organic phase; (3) separating the aqueous phase form the organic phase; (4) recovering the organic phase; and optionally, (5) removing a portion of water from the aqueous phase and thereafter repeating the steps of (2) to (5). The separation of step (3) is conducted by decantation, centrifugation, solvent extraction, chromatographic separation, or a combination of any two or more thereof, with decantation being preferred.

SUMMARY OF THE INVENTION

This invention provides a novel, highly efficient process enabling production of organic disulfides in high yield and purity. Not only is the process very easy and simple to carry out, but in addition the process (i) eliminates the need for forming an organic phase of liquid organic disulfide product and conducting a separation between such product and the total aqueous phase used in the reaction, (ii) enables efficient control of a highly exothermic reaction, and (iii) minimizes alkanesulfonic acid salt formation during the reaction.

In accordance with one of the embodiments of this invention there is provided a process for production of organic disulfide wherein an aqueous solution of basic mercaptide salt and water-soluble peroxide are contacted or mixed in a reaction zone under conditions effective to produce a vapor phase comprising organic disulfide, while concurrently recovering vapor phase from the reaction zone. Contact between the peroxide and the aqueous solution of basic mercaptide salt results in an exothermic reaction taking place. By maintaining a suitably low pressure in the reaction zone, a vapor phase comprising organic disulfide product is formed and concurrently removed or withdrawn from the reaction zone. This vaporization consumes a portion of the heat of reaction produced. At the same time by operating under suitable reaction temperature and pressure conditions, a portion of the water can be caused concurrently to vaporize from the aqueous solution in the reaction zone thereby further consuming the exothermic heat of reaction produced. Consequently, the temperature in the reaction zone is more readily controlled and maintained. Thus in the preferred modes of operation a vapor phase is formed comprising the organic disulfide being produced and water resulting from vaporization of a portion of aqueous reaction medium, and this vapor phase is removed (withdrawn or recovered) from the reaction zone concurrently with its formation, e.g., substantially as soon as it is formed.

It will be seen, therefore, that in conducting the process it is desirable to feed or introduce at a uniform or substantially uniform rate one of the reactants (i.e., the peroxide or the aqueous solution of basic mercaptide salt) into the reaction zone containing the other such reactant. Such feed rate preferably results, under the reaction conditions being used, in formation of vapor phase at a rate corresponding or substantially corresponding to the rate at which the vapor phase is being withdrawn from the reaction zone, thus providing and maintaining steady state conditions in the reaction zone. The feed itself can be intermittent or continuous. Preferably, the peroxide is fed into the aqueous solution of basic mercaptide salt, and preferably such feed is continuous during at least a major portion (more than 50%) of the reaction period. Most preferably, the continuous feed of peroxide is maintained during substantially the entire reaction period. Another way of conducting this reaction is to feed both reactants into the reaction zone at rates that result in formation of vapor phase at a rate corresponding or substantially corresponding to the rate at which the vapor phase is being withdrawn from the reaction zone, thereby providing and maintaining steady state conditions in the reaction zone.

Thus this invention provides, inter alia, a process for production of organic disulfide, which process comprises reacting mercaptide and peroxide in an aqueous reaction medium under conditions such that organic disulfide is formed and is vaporized, and concurrently recovering vapor phase comprising at least vaporized organic disulfide formed in the reaction, and preferably a vapor phase further comprising water vaporized from the aqueous reaction medium.

Another embodiment of this invention is a process for production of organic disulfide, which process comprises:

a) reacting a mercaptan with a base in an aqueous medium to form an aqueous solution of basic mercaptide salt;

b) contacting aqueous solution of basic mercaptide salt formed in a) and peroxide in a reaction zone under reaction conditions effective to produce a liquid aqueous reaction mixture and a vapor phase comprising organic disulfide; and c) concurrently withdrawing vapor phase from the reaction zone of b).

The withdrawn vapor phase is condensed and can be dried and purified in any suitable manner, but preferably is distilled. As noted above, preferably the withdrawn vapor phase comprises both vaporized organic disulfide product and vaporized water, and in such case the vapors are condensed to form a two-phase mixture of a predominately organic phase of organic disulfide and an aqueous phase of predominately water; and most preferably, these phases are separated from each other by gravity separation. The separated organic phase can then be further purified to achieve whatever final product purity is desired. A portion of the separated aqueous phase can be, and preferably is, recycled in amounts sufficient to maintain material and energy balance.

In each of the above embodiments, it is particularly preferred to utilize reaction conditions in the reaction between peroxide and mercaptide that cause or result in vaporization of liquid water from the reaction medium at a rate sufficient to consume in the range of about 50–100% of the exothermic heat of reaction resulting from the exothermic reaction that is occurring in that reaction zone. Also, additional heat above the heat of reaction can be put into the reactor, e.g., by means of a heating jacket, to effect even greater stripping of organic disulfide from the reactor. This minimizes the amount of dissolved disulfide in the aqueous phase which otherwise can react to form sulfonic acid with attendant losses of the desired product and of the inorganic base being used.

In conducting the process the amount of water present in the reaction mixture in b) should be at least sufficient to keep the reactants and reaction products in solution, but without use of an excessive amount of water above such amount. Thus it is desirable to proportion the feeds such that at the outset of the reaction between peroxide and mercaptide, the aqueous base solution contains about 15 wt % of the base such as sodium or potassium hydroxide, and to control the feeds such that the aqueous reaction solution contains no more than about 35 wt % of dissolved salts, and preferably in the range of about 20 to about 30 wt % of dissolved salts. Thus water can be fed to the reaction mixture in b) periodically as needed to maintain the reaction mixture in solution, and at least a portion of the water can be introduced as a peroxide solution, preferably as a solution of hydrogen peroxide.

Usually, the peroxide is introduced to the reaction mixture in the form of a solution, and typically as an aqueous solution which generally is in the range of a 1 to about 70% peroxide solution. In order to maintain a highly desirable material and energy balance in the reaction system of b), it is preferred to use a highly concentrated aqueous hydrogen peroxide solution, e.g., in the range of about 50 to about 70%, and to recycle a portion of the water recovered from the reaction mixture. This minimizes the amount of water that has to be disposed as plant effluent.

It is preferred to periodically discharge the entire reaction mass to purge out by-product sulfonic acid salt which will accumulate over time. Alternatively a continuous purge can be used to remove such by-product salt.

The above and other embodiments and features of this invention will be still further apparent from the ensuing description, the accompanying drawings, and the appended claims.

FURTHER DETAILED DESCRIPTION

Figure 1:
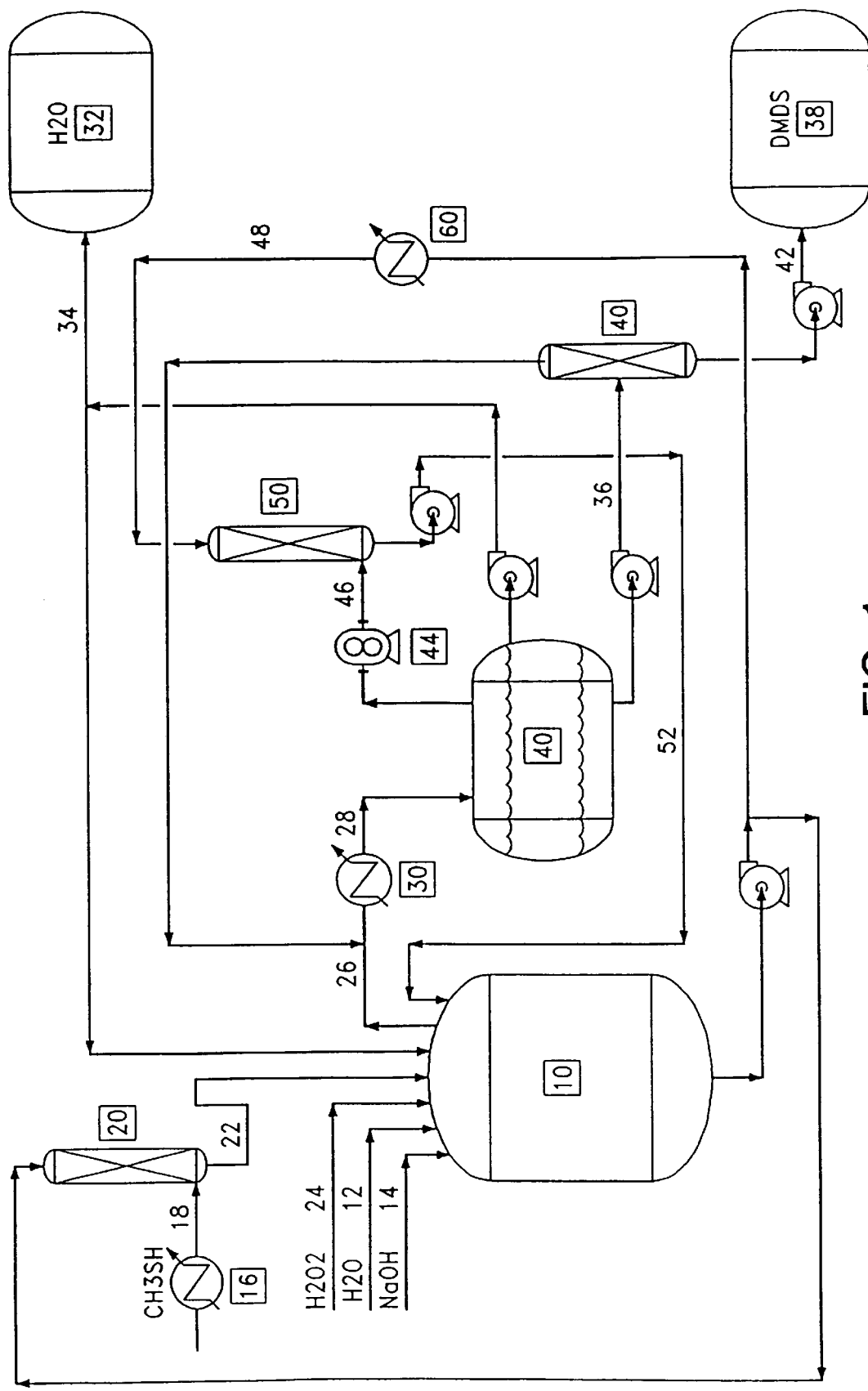
FIG. 1 is a schematic flow diagram of an installation for carrying out the process of this invention in a preferred manner on a semi-continuous basis.

For purposes of illustration, the operation of the installation depicted in FIG. 1 will be described with reference to production of dimethyl disulfide using sodium hydroxide and hydrogen peroxide as reagents in the process. It will be appreciated, however, that the same principles of operation can be utilized in the production of other suitably volatile organic disulfides. In the installation depicted, water and sodium hydroxide are fed to reactor 10 via lines 12 and 14, respectively, to produce a solution in the range of about 5 to about 20 wt %, preferably about 10 to 15 wt % NaOH. This solution is pumped to scrubber/neutralizer column 20, which preferably is fabricated from stainless steel or other suitable corrosion resistant material. Methyl mercaptan or other suitable hydrocarbyl mercaptan is vaporized in heat exchanger 16 and continuously fed via line 18 into column 20, where it reacts with the sodium hydroxide solution to form sodium mercaptide. Alternatively, the methyl mercaptan can be fed into column 20 in a liquid phase. Column 20 is operated at a pressure in the range of 0 to about 10 psig, and preferably in the range of about 1 to about 5 psig. The resulting aqueous reaction mixture containing sodium mercaptide and sodium hydroxide is transferred to reactor 10 via drain line 22.

An aqueous solution of hydrogen peroxide, preferably as an approximately 70% solution, is fed, preferably at a constant rate, via line 24 into reactor 10 where the sodium mercaptide is oxidized to dimethyl disulfide. In this operation reactor 10 is maintained at a temperature in the range of about 20 to about 110° C. and at a pressure in the range of about 50 to about 760 mm Hg (ca. 6.7 to about 101.3 kPa), and preferably at a temperature in the range of about 50 to about 75° C. and at a pressure in the range of about 140 to about 180 mm Hg (ca. 18.7 to about 24.0 kPa). The exothermic reaction typically provides sufficient heat energy under the conditions employed to flash the dimethyl disulfide from reactor 10 substantially as rapidly as it is being formed. In addition, under the conditions employed, a portion of the water is also being flashed from the reactor, and this is of material assistance in controlling the exothermic reaction taking place in reactor 10. The vapors exiting reactor 10 are transferred via line 26 to condenser 30 and the condensed liquids are transferred via line 28 to liquid/liquid separator 40 where the water and dimethyl disulfide phases are separated. The top phase is an aqueous phase typically substantially saturated with dimethyl disulfide (ca. 3000 ppm), and a portion is recycled back to reactor 10. A purge stream of the remainder of the aqueous phase is transferred to storage tank 32 via line 34. The dimethyl disulfide bottom phase, typically substantially saturated with water, is fed via line 36 to column 40 where the water content of the dimethyl disulfide is reduced from ca. 1300 ppm down to less than 50 ppm. During the distillation the dimethyl disulfide is not only dried but purified as well. The dry, purified dimethyl disulfide is sent to storage tank 38 via line 42.

Noncondensables, including methyl mercaptan, exiting condenser 30 and after leaving vacuum pump 44 are sent via line 46 to scrubber column 50. Column 50 is preferably fabricated from corrosion resistant material such as stainless steel. Scrubbing fluid for column 50 is pumped from reactor 10, through exchanger 60 and line 48 to column 50, and thereafter is returned to reactor 10 via line 52.

Mercaptide Formation

In the embodiments of this invention wherein the mercaptide is specifically formed for use in the process, the reaction can be illustrated using sodium hydroxide as the base, by the equation:

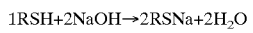

$$1RSH + 2NaOH \rightarrow 2RSNa + 2H_2O$$

Thus typically the reactants are fed in a ratio of about 0.8 to about 2 equivalents of base per mole of mercaptan. To minimize loss of volatile mercaptan in the vapor phase during the ensuing recovery of the organic disulfide product, it is preferred to use enough base in the mercaptide-forming reaction to provide in the range of about 0.1 to about 10 wt % excess, and more preferably in the range of about 0.1 to about 5 wt % excess, of free base over and above that consumed in forming the mercaptide. The base is typically employed as an aqueous solution.

Mercaptans useful in the process of this invention are typically hydrocarbyl mercaptans such as alkyl, cycloalkyl, aryl, and aralkyl mercaptans, which usually contain no more than about 10 carbon atoms. Preferred reactants are alkyl mercaptans having up to about four carbon atoms, with methyl mercaptan and ethyl mercaptan being particularly preferred. The operating temperature and pressure should be adjusted such that the resulting disulfide is substantially vaporized in the reactor as it is formed. Thus if the mercaptan has a relatively high boiling point, a lower pressure or higher temperature, or both, should be used.

The base used in forming the aqueous basic or alkaline solutions used in forming the mercaptide is an inorganic base such as an alkali metal oxide, hydroxide, carbonate, bicarbonate, amide, or other basic salt, or an alkaline earth metal oxide, hydroxide, carbonate, bicarbonate, amide, or other basic salt. Examples include sodium oxide, sodium hydroxide, potassium oxide, potassium hydroxide, potassium carbonate, calcium oxide, calcium hydroxide, barium hydroxide, and like bases. Preferred are sodium hydroxide, potassium hydroxide, sodium oxide, and potassium oxide. In other words, aqueous solutions of sodium hydroxide and potassium hydroxide are preferred.

If the basicity of the aqueous solution used in the mercaptide forming step is relatively high and the aqueous solution is not diluted before conducting the peroxide oxidation, there is a possibility that some of the peroxide will be prematurely decomposed when performing the peroxide oxidation reaction. In such cases, the concentration of the aqueous base solution in the mercaptide-forming step when using a strong base such as sodium hydroxide or potassium hydroxide is typically kept in the range of about 2 to about 50 wt %, and preferably in the range of about 5 to about 15 wt %.

The mercaptide-forming step can be conducted under any suitable temperature and pressure conditions. Typically, temperatures in the mercaptide-forming reaction are in the range of about 20 to about 100° C. The pressure at which the reaction is performed is largely discretionary—the reaction can be performed at atmospheric pressure, at sub-atmospheric pressure or at super-atmospheric pressure.

Organic Disulfide Formation

This reaction is illustrated by the following equation for the reaction between a sodium mercaptide and hydrogen peroxide:

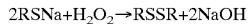

2RSNa+H$_2$O$_2$→RSSR+2NaOH

In general, therefore the reactants in this process are typically fed to the reactor in a ratio of about 0.05 to about 0.5 equivalents of peroxide per equivalent of mercaptide, including recycled mercaptide, if recycle is used. Overall about 0.5 mole of hydrogen peroxide is consumed per mole of the mercaptide.

In the mercaptide oxidation reaction, peroxide is typically used as the oxidant although other peroxy compounds such as hydroperoxides, persulfates, peroxycarbonates, superoxides, and like substances may be useable in lieu of peroxide or in addition thereto. Use of inorganic peroxides such as sodium peroxide, inorganic peroxy-acids (e.g., peroxystannic acid, peroxyvanadic acid, etc.), barium peroxide, zinc peroxide, thorium peroxide, and especially hydrogen peroxide, is preferable as such materials do not contribute organic residues to the reaction mixture and thus purification of the organic disulfide is facilitated. However it is within the scope of this invention to use an organic peroxide, if desired. When using hydrogen peroxide, it is preferably employed as a 10 to 70% or more aqueous solution, and 50 to 70% aqueous hydrogen peroxide solutions are most preferred.

While the mercaptide reaction mixture and the peroxide can be mixed together in any suitable manner, it is preferable to introduce the peroxide into the aqueous mercaptide reaction product mixture or into a freshly-prepared aqueous solution of the mercaptide at a controlled, extended rate of addition to prevent the virtually instantaneous, highly exothermic reaction from becoming excessively hot and uncontrollable. The controlled addition itself can be continuous or discontinuous, or a combination of both modes of addition of the peroxide. The reaction should be conducted at a reduced pressure sufficiently low, and the temperature should be controlled and maintained, such that the organic disulfide product being formed will vaporize from the reaction mixture essentially as soon as it is formed. Likewise, the conditions used preferably enable a portion of the water in the reaction mixture to vaporize along with the organic disulfide to thereby help maintain a well-controlled exothermic reaction under more-or-less steady state conditions. Typically the temperatures will be maintained within the range of about 20 to about 110° C., with pressures in the range of about 50 to about 760 mm Hg. It will be understood and appreciated that on the basis a reading and an understanding of this disclosure, it is now possible for departures to be made from the foregoing ranges of temperature and/or pressure whenever deemed necessary or desirable by those skilled in the art without departing from the spirit and scope of this invention.

Concurrent Reactions

In the embodiments of this invention wherein the mercaptide is specifically formed for use in the process, the mercaptide formation reaction and the mercaptide oxidation reaction to form the disulfide product in many cases can be performed concurrently in the same reaction vessel. This is accomplished by concurrently feeding all of the reaction components to the reactor and adjusting and maintaining the reaction conditions as described above such that the reactions identified at the outset as a) and b) occur concurrently. It is believed that as soon as the mercaptide is formed in situ, it is oxidized to the disulfide.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for production of organic disulfide, which process comprises contacting an aqueous solution of basic mercaptide salt and water-soluble peroxide in a reaction zone and under reaction conditions effective to produce a vapor phase comprising organic disulfide without forming an organic phase of liquid organic disulfide product, and concurrently recovering vapor phase from the reaction zone.

2. A process according to claim 1 wherein said vapor phase also comprises vaporized water.

3. A process according to claim 2 wherein said peroxide is hydrogen peroxide.

4. A process according to claim 2 wherein said basic mercaptide salt is an alkali metal mercaptide salt.

5. A process according to claim 4 wherein said peroxide is hydrogen peroxide.

6. A process according to claim 2 wherein said basic mercaptide salt is sodium methyl mercaptide or sodium ethyl mercaptide.

7. A process according to claim 6 wherein said peroxide is hydrogen peroxide.

8. A process for production of organic disulfide, which process comprises:
    a) reacting a mercaptan with a base in an aqueous medium to form an aqueous solution of basic mercaptide salt;
    b) contacting aqueous solution of basic mercaptide salt formed in a) and peroxide in a reaction zone under reaction conditions effective to produce a vapor phase comprising organic disulfide without forming an organic phase of liquid organic disulfide product; and
    c) concurrently withdrawing vapor phase from the reaction zone of b).

9. A process according to claim 8 wherein said vapor phase also comprises vaporized water.

10. A process according to claim 9 wherein said peroxide is hydrogen peroxide.

11. A process according to claim 9 wherein said base is an alkali metal base and said basic mercaptide salt is an alkali metal mercaptide salt.

12. A process according to claim 11 wherein said peroxide is hydrogen peroxide.

13. A process according to claim 9 wherein said mercaptan is methyl mercaptan or ethyl mercaptan, wherein said base is a basic inorganic sodium compound, and wherein said basic mercaptide salt is sodium methyl mercaptide or sodium ethyl mercaptide.

14. A process according to claim 13 wherein said peroxide is hydrogen peroxide.

15. A process according to claim 8 wherein said reaction conditions in b) are such as to cause vaporization of liquid water from the reaction medium at a rate sufficient to consume at least 50% of the exothermic heat of reaction resulting from the reaction that occurs in b).

16. A process according to claim 15 wherein the aqueous solution of basic mercaptide salt formed in a) is an aqueous solution of alkali metal methyl mercaptide or alkali metal ethyl mercaptide, and wherein the peroxide in the form used in b) is hydrogen peroxide or an aqueous solution thereof.

17. A process according to claim 8 wherein heat energy is supplied to the reaction mixture over and above the exothermic heat of reaction resulting from said reaction.

18. A process according to claim 8 wherein a) and b) are conducted concurrently in the same reactor.

19. A process for production of organic disulfide, which process comprises reacting mercaptide and peroxide in an aqueous reaction medium under conditions such that organic disulfide is formed and is vaporized concurrently without forming an organic phase of liquid organic disulfide product, and concurrently recovering vapor phase comprising vaporized organic disulfide formed in the reaction.

20. A process according to claim 19 wherein said vapor phase also contains water vapor.

21. A process according to claim 19 wherein said conditions are such as to cause vaporization of liquid water from the reaction medium at a rate sufficient to consume at least 50% of the exothermic heat of reaction resulting from said reaction.

22. A process according to claim 21 wherein the mercaptide in the form fed to the reaction is a basic mercaptide salt or an aqueous solution thereof, and wherein the peroxide in the form fed to the reaction is hydrogen peroxide or an aqueous solution thereof.

23. A process according to claim 19 wherein heat energy is supplied to the reaction mixture over and above the exothermic heat of reaction resulting from said reaction.

24. A process for production of dimethyl disulfide, which process comprises:
    i) feeding hydrogen peroxide intermittently or continuously into an aqueous solution of alkali metal methyl mercaptide in a reaction zone under reaction conditions effective to produce a vapor phase comprising dimethyl disulfide without forming an organic phase of liquid dimethyl disulfide product; and
    ii) withdrawing vapor phase from the reaction zone of i) at one or more rates equivalent or substantially equivalent to the rate at which vapor phase is being formed by the reaction occurring in the reaction zone of i).

25. A process according to claim 24 wherein said vapor phase also contains water vapor.

26. A process according to claim 24 wherein said reaction conditions are such as to cause vaporization of liquid water from the reaction medium at a rate sufficient to consume at least 50% of the exothermic heat of reaction resulting from said reaction.

27. A process according to claim 24 wherein heat energy is supplied to the reaction mixture over and above the exothermic heat of reaction resulting from said reaction.

28. A process according to claim 24 wherein:
    A) the hydrogen peroxide used in i) is approximately 70% aqueous hydrogen peroxide;
    B) the alkali metal methyl mercaptide used in i) is an aqueous solution of sodium methyl mercaptide;
    C) the reaction conditions in i) include one or more temperatures in the range of about 55 to about 65° C. and one or more pressures in the range of about 140 to about 180 mm Hg, absolute;
    D) the hydrogen peroxide is fed at a constant or substantially constant flow rate;
    E) the vapor phase withdrawn from the reaction zone of i) is condensed to form a two-phase liquid mixture of a predominately organic phase of dimethyl disulfide and an aqueous phase of predominately water; and
    F) the phases formed in E) are separated from each other.

29. A process according to claim 28 wherein aqueous phase separated in F) is recycled to i).

30. A process according to claim 28 wherein dimethyl disulfide of the organic phase separated in F) is concurrently dried and purified by subjecting said organic phase to distillation.

31. A process according to claim 24 wherein the aqueous solution of alkali metal methyl mercaptide of i) is formed by reacting methyl mercaptan with alkali metal base dissolved in an aqueous medium.

32. A process according to claim 25 wherein the aqueous solution of alkali metal methyl mercaptide of i) is formed by feeding methyl mercaptan into an aqueous solution of alkali metal base.

33. A process according to claim 26 wherein the aqueous solution of alkali metal methyl mercaptide of i) is formed by feeding methyl mercaptan into an aqueous solution of alkali metal base.

34. A process according to claim 28 wherein the aqueous solution of sodium methyl mercaptide is formed by reacting methyl mercaptan with an inorganic sodium base dissolved in an aqueous medium.

35. A process according to claim 29 wherein the aqueous solution of sodium methyl mercaptide is formed by feeding methyl mercaptan into an aqueous solution of an inorganic sodium base.

36. A process according to claim 30 wherein the aqueous solution of sodium methyl mercaptide is formed by feeding methyl mercaptan into an aqueous solution of an inorganic sodium base.

37. A process for production of dimethyl disulfide, which process comprises mixing together 50 to 70% aqueous hydrogen peroxide and an aqueous solution of sodium methyl mercaptide or potassium methyl mercaptide in a reaction zone and under reaction conditions effective to produce a vapor phase comprising dimethyl disulfide without forming an organic phase of liquid dimethyl disulfide product, and concurrently recovering vapor phase from the reaction zone.

38. A process according to claim 37 wherein the reaction conditions include one or more reaction temperatures in the range of about 55 to about 65° C. and one or more pressures in the range of about 140 to about 180 mm Hg, absolute.

39. A process according to claim 37 wherein the vapor phase recovered from the reaction zone is condensed to form a two-phase liquid mixture of a predominately organic phase of dimethyl disulfide and an aqueous phase of predominately water, and wherein said phases are separated from each other.

40. A process according to claim 37 wherein the reaction conditions include one or more reaction temperatures in the range of about 55 to about 65° C. and one or more pressures in the range of about 140 to about 180 mm Hg, absolute; wherein the vapor phase recovered from the reaction zone is condensed to form a two-phase liquid mixture of a predominately organic phase of dimethyl disulfide and an aqueous phase of predominately water; wherein said phases are separated from each other; and wherein the separated organic phase is distilled so as to isolate dimethyl disulfide in dried, purified form.

* * * * *